United States Patent [19]

Ferrini

[11] Patent Number: 5,051,421
[45] Date of Patent: Sep. 24, 1991

[54] BENZO-[B]THIOPHENE DERIVATIVES

[75] Inventor: Pier G. Ferrini, Binningen, Switzerland

[73] Assignee: Ciba-Geigy Corporation, Ardsley, N.Y.

[21] Appl. No.: 467,088

[22] Filed: Jan. 18, 1990

Related U.S. Application Data

[62] Division of Ser. No. 324,367, Mar. 15, 1989, abandoned.

[30] Foreign Application Priority Data

Mar. 16, 1988 [CH] Switzerland ............... 998/88

[51] Int. Cl.$^5$ ................. C07D 409/06; C07D 403/06; C07D 237/06; C07D 285/06; C07D 285/14; C07D 277/30; A61K 31/335; A61K 31/38; A61K 31/44; A61K 31/495
[52] U.S. Cl. .................... 514/245; 514/241; 514/247; 514/255; 514/269; 514/272; 514/337; 514/362; 514/363; 514/364; 514/372; 514/374; 514/377; 514/378; 514/359; 514/380; 514/383; 514/397; 514/406; 514/407; 514/422; 514/365; 514/370; 514/443; 544/198; 544/209; 544/212; 544/238; 544/324; 544/328; 544/331; 544/333; 544/405; 546/274; 548/127; 548/128; 548/134; 548/136; 548/138; 548/125; 548/131; 548/133; 548/143; 548/190; 548/191; 548/194; 548/204; 548/215; 548/233; 548/235; 548/236; 548/245; 548/253; 548/255; 548/262; 548/266; 548/267; 548/336; 548/374; 548/525; 549/52; 549/53; 549/54; 549/55; 549/56
[58] Field of Search ............... 544/209, 212, 216, 217; 514/241, 245

[56] References Cited

U.S. PATENT DOCUMENTS 3,558,616  1/1971  Brandstrom et al. ............ 260/247.1
3,594,478  7/1971  Brandstrom et al. ............... 424/248
4,514,415  4/1985  Wenk et al. .......................... 514/470
4,663,344  5/1987  Durette et al. ...................... 514/443

OTHER PUBLICATIONS

Chem. Abstracts Formula Index C$_{16}$-Z, vol. 78, 1245F (1973).
Tetrahedron, vol. 29, p. 321 (1973).
Chemical Abstract, vol. 95, 7016e (1981).
Chem. Abstract, vol. 78, 135981b (1973).

Primary Examiner—Johann Richter
Attorney, Agent, or Firm—JoAnn Villamizar

[57] ABSTRACT

Benzo[b]thiophene derivatives of formula

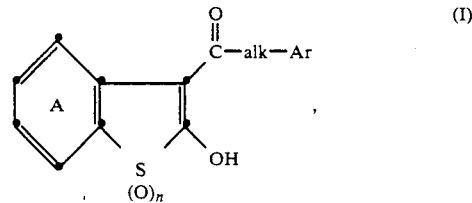

their tautomers and salts, in which the index n is 0, 1 or 2, alk is lower alkylene, Ar is phenyl, naphthyl or a monocyclic, five- or six-membered heteroaryl radical, wherein the aromatic radical is unsubstituted or is mono- or poly-substituted by lower alkyl, halo-lower alkyl, halogen and/or by nitro, and the ring A is unsubstituted or is mono- or poly-substituted by lower alkyl, lower alkoxy, lower alkylthio, lower alkanesulfinyl, lower alkanesulfonyl, halo-lower alkyl, halogen and/or by nitro, can be used, for example, as active ingredients in medicaments.

4 Claims, No Drawings

BENZO-[B]THIOPHENE DERIVATIVES

This is a divisional of application Ser. No. 324,367 filed on Mar. 15, 1989, now abandoned.

The invention relates to novel benzo[b]thiophene derivatives of formula

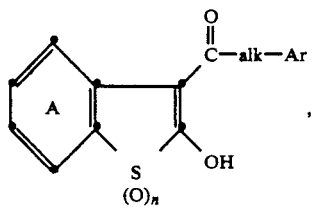

their tautomers and salts, in which the index n is 0, 1 or 2, alk is lower alkylene, Ar is phenyl, naphthyl or a monocyclic, five- or six-membered heteroaryl radical, wherein the aromatic radical is unsubstituted or is mono- or poly-substituted by lower alkyl, halo-lower alkyl, halogen and/or by nitro, and the ring A is unsubstituted or is mono- or poly-substituted by lower alkyl, lower alkoxy, lower alkylthio, lower alkanesulfinyl, lower alkanesulfonyl, halo-lower alkyl, halogen and/or by nitro, to processes for their preparation, to their use, and to pharmaceutical preparations containing these compounds and the manufacture thereof.

The free compounds of formula I can be in dynamic equilibrium with corresponding tautomers. The 2-hydroxy-benzo[b]thiophene derivatives of formula I can therefore be in the form of 2-oxo-2,3-dihydro-benzo[b]thiophene compounds of formula Ia

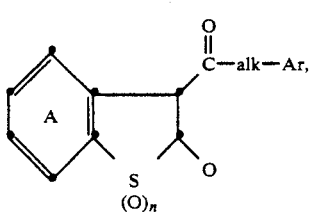

but the equilibrium predominantly favours the corresponding 2-hydroxy-benzo[b]thiophene tautomers.

The compounds of formulae I and Ia can also form salts, especially salts with bases, the salt formation being effected with the acidic oxygen function in the 2-position of the benzo[b]thiophene ring. Corresponding salts are, for example, metal salts, such as alkali metal or alkaline earth metal salts, for example sodium, potassium, magnesium or calcium salts, aluminium or transition metal salts, such as zinc or copper salts, or corresponding salts with ammonia or organic amines. Examples of organic amines that come into consideration are: alkylamines, such as mono-, di- or tri-lower alkylamines, alkylenediamines, such as lower alkylenediamines, phenyl-substituted alkylamines, such as mono- or di-phenyl-lower alkylamines, hydroxyalkylamines, such as mono-, di- or tri-hydroxy-lower alkylamines, an oligohydroxy-lower alkylamine or hydroxy-lower alkyl-di-lower alkylamine, amino sugars, for example those of which the amino group can optionally be substituted by at least one lower alkyl radical, cycloalkylamines, such as mono- or di-cyclo-lower alkylamines, basic amino acids, cyclic amines, such as lower alkylene- or lower alkenylene-amines having from 2 to 6 carbon atoms, it being possible for the carbon chain also to be interrupted by aza, N-lower alkyl-aza, oxa and/or by thia. Mono-, di- or tri-lower alkylamines are, for example, ethyl- or tert.-butyl-amine, diethyl- or diisopropyl-amine, trimethyl- or triethyl-amine, and lower alkylenediamine is, for example, ethylenediamine. Phenyl-lower alkylamines that come into consideration are, for example, benzyl- or 1- or 2-phenylethyl-amine. Mono-, di- or tri-hydroxy-lower alkylamines are, for example, mono-, di- or tri-ethanolamine or diisopropanolamine, an oligo-hydroxy-lower alkylamine, for example tris-(hydroxymethyl)methylamine, and hydroxy-lower alkyl-di-lower alkylamines, for example N,N-dimethyl- or N,N-diethyl-aminoethanol. Amino sugars are derived, for example, from monosaccharides in which an alcoholic hydroxy group has been replaced by an amino group, such as D-glucosamine, D-galactosamine or marmosamine. An example of an N-lower alkylated amino sugar that may be mentioned is N-methyl-D-glucosamine. Mono- or di-cyclo-lower alkylamine is, for example, cyclohexyl- or dicyclohexylamine. Basic amino acids are, for example, arginine, histidine, lysine or ornithine. Lower alkylene- and lower alkenylene-amines are, for example, azirine, pyrrolidine, piperidine or pyrroline, and suitable lower alkylene- and lower alkenylene-amines of which the carbon chain is interrupted by aza, N-lower alkylaza, oxa and/or by thia are, for example, imidazoline, 3-methylimidazoline, piperazine, 4-methyl- or 4-ethyl-piperazine, morpholine or thiomorpholine. Preferred are pharmaceutically acceptable salts, e.g. alkali metal salts, such as sodium salts.

The variable alk is especially —CH(R)— in which R is lower alkyl or hydrogen.

Monocyclic five-membered heteroaryl radicals are, for example, corresponding monoaza-, diaza-, triaza-, tetraaza-, monooxa-, monothia-, oxaza-, oxadiaza-, thiaza- or thiadiaza-cyclic radicals, such as pyrrolyl, pyrazolyl, imidazolyl, triazolyl, tetrazolyl, furyl, thienyl, isoxazolyl, oxazolyl, oxadiazolyl, isothiazolyl, thiazolyl or thiadiazolyl.

Monocyclic six-membered heteroaryl radicals are, for example, corresponding monoaza-, diaza- or triaza-cyclic radicals, such as pyridyl, pyridazinyl, pyrimidinyl, pyrazinyl or triazinyl; pyridyl radicals can also be in the form of 1-oxidopyridyls.

In corresponding five- or six-membered heteroaryl radicals that have an —NH group, the hydrogen atom concerned can be substituted by lower alkyl. Examples of such radicals Ar that may be mentioned are 1-lower alkylpyrrolyl, such as 1-methylpyrrol-2-yl, or 1-lower alkylimidazoyl, such as 1-methylimidazol-2-yl.

The ring A and the radical Ar can especially be unsubstituted or may be mono-substituted, also polysubstituted, for example di- or tri-substituted.

Unless defined otherwise, the general definitions used hereinbefore and hereinafter have especially the following meanings:

The term "lower" means that the groups or compounds so designated contain especially up to and including 7, preferably up to and including 4, carbon atoms.

Lower alkylene is straight-chain or branched and is, for example, methylene, ethylene, 1-methylmethylene, and also 1- or 2-methylethylene, propylene or butylene.

Lower alkyl is, for example, methyl, ethyl, n-propyl, isopropyl, n-butyl, isobutyl, sec.-butyl, tert.-butyl, and also includes corresponding pentyl, hexyl and heptyl radicals.

Halo-lower alkyl is, for example, trifluoromethyl, 1,1,2-trifluoro-2-chloroethyl or chloromethyl.

Halogen is especially halogen having an atomic number of up to and including 35, such as fluorine, chlorine or bromine, and also includes iodine.

Lower alkoxy is, for example, methoxy, ethoxy, n-propoxy, isopropoxy, n-butoxy, isobutoxy, sec.-butoxy, tert.-butoxy, and also includes corresponding pentyloxy, hexyloxy and heptyloxy radicals.

Lower alkylthio is, for example, methyl-, ethyl-, n-propyl-, isopropyl-, n-butyl-, isobutyl-, sec.-butyl- or tert.-butyl-thio.

Lower alkane-sulfinyl or -sulfonyl is, for example, methane-, ethane-, n-propane- or isopropane-sulfinyl or -sulfonyl.

The compounds of formula I and Ia and their pharmaceutically acceptable salts have, for example, valuable pharmacological properties. For example, they exhibit, especially, pronounced analgesic properties which can be deduced, for example, from the reduction in the phenyl-p-benzoquinone-induced Writhing Syndrome in mice at a dose of approximately 0.1 mg/kg and above p.o. [procedure: L. C. Hendershot and J. Forsaith, J. Pharmacol. exp. Ther. 125, 237 ff (1959) and A. Schweizer et al., Agents and Actions 23, 1/2 (1988) in press]. Likewise, in the experimental arrangement according to Pain Res. and Therap., Vol. 1, 517 ff (1976), Raven Press N.A., the compounds according to the invention bring about an inhibition of the acetic acid-induced Writhing Syndrome in rats at a dose of approximately 1 mg/kg and above p.o.. Advantageously, the analgesic activity is exhibited over a prolonged time period so that administrations can be made less frequently.

Furthermore, the compounds according to the invention have surprisingly good gastro-intestinal tolerability, which in turn results in a broad therapeutic spectrum. For example, in accordance with the procedure of I. Böttcher et al., Drugs exp. clin. Res. 13, 237 ff (1987) the gastro-intestinal blood loss in rats was investigated during 10 days' treatment with the active ingredients, and it was shown that a slight increase in the tendency towards bleeding exceeding that to be observed in untreated rats was detected only at dosages in the range of approximately from 50 to 200 mg/kg p.o.

Furthermore, the compounds according to the invention exhibit significant inhibitory effects on cyclooxygenase and at the same time 5-lipoxygenase. Inhibitors of both enzymes can be used for the treatment of inflammatory processes.

Accordingly, the compounds of formulae I and Ia and their pharmaceutically acceptable salts can be used, for example, as (peripheral) analgesics and antiinflammatorey agents for the treatment of pain and inflammations. The invention relates also to the use of the compounds according to the invention for the therapeutic and/or prophylactic treatment of the human and animal body, especially for the treatment of pain and inflammations, and to the use thereof for the manufacture of medicaments, especially analgesics. The commercial formulation of the active ingredients is also included.

The invention relates especially to compounds of formulae I and Ia and their salts, in which the index n is 0, 1 or 2, alk is lower alkylene, especially —CH(R)— and R is hydrogen or lower alkyl, Ar is phenyl, naphthyl, pyrrolyl, pyrazolyl, imidazolyl, triazolyl, tetrazolyl, furyl, thienyl, isoxazolyl, oxazolyl, oxadiazolyl, isothiazolyl, thiazolyl, thiadiazolyl, pyridyl, pyridazinyl, pyrimidinyl, pyrazinyl or triazinyl, each of which is unsubstituted or is mono- or poly-substituted by lower alkyl, halo-lower alkyl, halogen and/or by nitro, and in corresponding heteroaryl radicals having the —NH group, the hydrogen atom concerned can be substituted by lower alkyl, and the ring A is unsubstituted or is mono- or poly-substituted by lower alkyl, lower alkoxy, lower alkylthio, lower alkanesulfinyl, lower alkanesulfonyl, halo-lower alkyl, halogen and/or by nitro.

The invention relates especially to compounds of formulae I and Ia and their salts, in which the index n is 0, 1 or 2, Ar is phenyl, naphthyl, pyrrolyl, pyrazolyl, imidazolyl, triazolyl, tetrazolyl, furyl, thienyl, isoxazolyl, oxazolyl, oxadiazolyl, isothiazolyl, thiazolyl, thiadiazolyl, pyridyl, pyridazinyl, pyrimidinyl, pyrazinyl or triazinyl, each of which is unsubstituted or is mono- or poly-substituted by lower alkyl, halo-lower alkyl, halogen and/or by nitro, the ring A is unsubstituted or is mono- or poly-substituted by lower alkyl, lower alkoxy, lower alkylthio, lower alkanesulfinyl, lower alkanesulfonyl, halo-lower alkyl, halogen and/or by nitro, and alk is —CH(R)— in which R is hydrogen or lower alkyl.

The invention relates especially to compounds of formulae I and Ia and their salts, in which the index n is 0, also 1 or 2, alk is lower alkylene, especially —CH(R)— and R is hydrogen or lower alkyl, Ar is phenyl, pyrrolyl, 1-lower alkylpyrrolyl, thienyl, thiazolyl or pyridyl, each of which is unsubstituted or is mono- or poly-substituted by lower alkyl, lower alkoxy, halo-lower alkyl, especially trifluoromethyl, or by halogen, and the ring A is unsubstituted or is mono- or poly-substituted by lower alkyl, lower alkoxy, halo-lower alkyl, especially trifluoromethyl, halogen or by nitro.

The invention relates especially to compounds of formulae I and Ia and their salts, in which the index n is 0, 1 or 2, alk is —CH(R)— and R is hydrogen or lower alkyl, Ar is phenyl, pyrrolyl, thienyl or pyridyl, each of which is unsubstituted or is mono- or poly-substituted by halo-lower alkyl, especially trifluoromethyl, or by halogen, and the ring A is unsubstituted or is mono- or poly-substituted by lower alkyl, lower alkoxy, halo-lower alkyl, especially trifluoromethyl, halogen or by nitro.

The invention relates especially to compounds of formulae I and Ia and their salts, in which the index n is 0, alk is —CH(R)— and R is lower alkyl, especially having up to and including 4 carbon atoms, such as methyl, Ar is phenyl, thiazolyl, such as 2-thiazolyl, or pyridyl, such as 2-pyridyl, each of which is unsubstituted or is substituted by lower alkoxy, especially having up to and including 4 carbon atoms, such as methoxy, halogen, especially having an atomic number of up to and including 35, such as fluorine or chlorine, or by trifluoromethyl, in each case located especially in the 3- or 4-position, or Ar is unsubstituted 1-lower alkylpyrrolyl, especially having up to and including 4 carbon atoms in the lower alkyl moiety, such as 1-methylpyrrol-2-yl, or thienyl, such as 2- or 3-thienyl, which is unsubstituted or is substituted by lower alkyl, especially having up to and including 4 carbon atoms, such as methyl, or halogen, especially having an atomic number of up to and including 35, such as bromine, and the ring A is unsubstituted or is substituted, especially in the 5- or 6-position of the ring system, by halogen, especially having an atomic number of up to and including 35, such as fluorine or chlorine, or by nitro.

The invention relates especially to compounds of formulae I and Ia and their salts, in which the index n is 0, also 1 or 2, alk is —CH(R)— and R is hydrogen or lower alkyl, especially having up to and including 4 carbon atoms, Ar is phenyl that is unsubstituted or is substituted by halo-lower alkyl, especially having up to and including 2 carbon atoms, such as trifluoromethyl, or by halogen, especially having an atomic number of up to and including 35, such as fluorine or chlorine, or Ar is unsubstituted pyrrolyl, thienyl or pyridyl, and the ring A is unsubstituted or is monosubstituted by halogen, especially having an atomic number of up to and including 35, such as florine or chlorine, or by nitro.

The invention relates more especially to compounds of formulae I and Ia and their salts, in which the index n is 0, alk is —CH(R)— and R is hydrogen, Ar is phenyl that is unsubstituted or is substituted by trifluoromethyl or by halogen having an atomic number of up to and including 35, such as florine, especially in the 3- or 4-position, or Ar is unsubstituted thienyl, such as 2-thienyl, and the ring A is unsubstituted or is substituted by halogen having an atomic number of up to and including 35, such as fluorine, especially in the 5- or 6-position of the ring system.

The invention relates more especially to compounds of formulae I and Ia and their salts, in which the index n is 0, alk is —CH(R)— and R is hydrogen, Ar is phenyl or 2- or 3-thienyl, and the ring A is unsubstituted or is substituted in the 5- or 6-position of the ring system by fluorine or chlorine.

The invention relates more especially to compounds of formulae I and Ia and their salts, in which the index n is 0, alk is —CH(R)— and R is hydrogen, Ar is thienyl, such as 2-thienyl, and the ring A is unsubstituted or is substituted by fluorine, especially in the 5- or 6-position of the ring system.

The invention relates especially to the novel compounds mentioned in the Examples and to their preparation.

The invention relates also to processes for the preparation of the compounds according to the invention. The preparation of the compounds of formula I, their tautomers and their salts is effected in a manner known per se and is carried out, for example, as follows:

a) a compound of formula

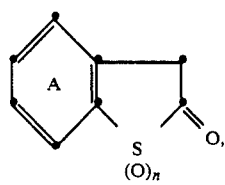

(IIa)

a tautomer or salt thereof, is reacted with a compound of the formula $X_1$-CO-alk-Ar (IIb) in which $X_1$ is reactive esterified hydroxy, or b) a compound of formula

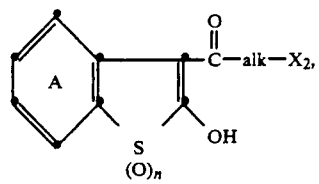

(IIIa)

a tautomer or salt thereof, in which $X_2$ is reactive esterified hydroxy, is reacted with a compound of formula Ar-H (IIIb), and, if desired, a compound obtainable in accordance with the process or by other means is converted into a different compound of formula I or Ia, respectively, an isomeric mixture obtainable in accordance with the process is separated into the components, a free compound of formula I or Ia, respectively, obtainable in accordance with the process is converted into a salt and/or a salt obtainable in accordance with the process is converted into the free compound of formula I or Ia, respectively, or into a different salt.

The reactions described in the variants hereinbefore and hereinafter are carried out in a manner known per se, for example in the absence or usually in the presence of a suitable solvent or diluent or a mixture thereof, the reactions being carried out, as necessary, with cooling, at room temperature or with heating, for example in a temperature range of from approximately −78° C. to the boiling temperature of the reaction medium, preferably from approximately −10° to approximately 150° C., and, if necessary, in a closed vessel, under pressure, in an inert gas atmosphere and/or under anhydrous conditions.

The starting materials of formulae IIa and IIb and IIIa and IIIb given hereinbefore and hereinafter, which have been developed for the preparation of the compounds of formula I, their tautomers and salts, are known in some cases or they can be prepared by methods known per se, for example analogously to the process variants described above.

Free compounds of formulae IIa and IIIa can also be in the form of the corresponding tautomers, for example compounds of formula IIa can be in the form of the corresponding 2-hydroxy-benzo[b]thiophenes and compounds of formula IIIa can be in the form of the corresponding 2-oxo-2,3-dihydrobenzo[b]thiophene tautomers, in which case, for example, in the case of the compounds of formula IIa the equilibrium preferentially favours the 2-oxo-benzo[b]thiophene form and in the case of compounds of formula IIIa the equilibrium preferentially favours the 2-hydroxy-benzo[b]thiophene form.

The starting materials of formulae IIa and IIIa can form, for example, salts with bases, for example those of the kind mentioned in connection with the compounds of formula I, the salt formation being effected with the acidic oxygen function in the 2-position of the ring system.

Within the scope of the process description hereinbefore and hereinafter, unless defined otherwise, reactive esterified hydroxy, for example $X_1$, is especially hydroxy esterified by a strong inorganic acid, organic sulfonic acid, organic carboxylic acid or carbonic acid, for example halogen, such as chlorine, bromine or iodine, sulfonyloxy, such as hydroxysulfonyloxy, halosulfonyloxy, for example fluorosulfonyloxy, lower alkanesulfonyloxy that is unsubstituted or substituted, for example by halogen, for example methane- or trifluoromethane-sulfonyloxy, $C_3$–$C_7$cycloalkanesulfonyloxy, for example cyclohexanesulfonyloxy, or benzenesulfonyloxy that is unsubstituted or substituted, for example by lower alkyl or by halogen, for example p-bromophenyl- or p-toluene-sulfonyloxy, lower alkanoyloxy that is unsubstituted or substituted, for example by halogen, such as acetyl- or trifluoro-acetoxy, benzoyloxy that is unsubstituted or substituted, for example by lower alkyl, lower alkoxy, halogen and/or by nitro, or lower alkoxycarbonyloxy, such as isobutoxycarbonyloxy.

Variant a)

$X_1$ is especially halogen, such as chlorine.

The reaction according to the process is carried out in a manner known per se, especially in the presence of a base.

Suitable bases are, for example, alkali metal hydroxides, hydrides, amides, alkanolates, carbonates, triphenylmethylides, di-$C_1$–$C_7$alkylamides, amino-$C_1$–$C_7$alkylamides or $C_1$–$C_7$alkylsilylamides, or naphthaleneamines, $C_1$–$C_7$alkylamines, basic heterocycles, ammonium hydroxides and carbocyclic amines. Examples that may be mentioned are lithium hydroxide, sodium hydroxide, hydride, amide or ethanolate, potassium tert.-butanolate or carbonate, lithium triphenylmethylide or diisopropylamide, potassium 3-(aminopropyl)-amide or bis-(trimethylsilyl)-amide, or dimethylaminonaphthalene, di- or tri-ethylamine, pyridine, benzyltrimethylammonium hydroxide, 1,5-diazabicyclo[4.3.0]-non-5ene (DBN) and 1,8-diazabicyclo[5.4.0]undec-7-ene (DBU).

The starting materials to be used in this process variant are known in some cases or they can be prepared in a manner known per se.

Variant b)

$X_2$ is especially halogen, such as chlorine, and lower alkoxycarbonyloxy, such as isobutoxycarbonyloxy.

The alkylation of compounds of formula IIIb is carried out according to methods known per se, especially in the presence of a Lewis acid or an adduct, such as an etherate, thereof. Suitable Lewis acids are, for example, halides of boron, phosphorus, arsenic, antimony, tin, silver, zinc or iron, such as $BF_3$, $AlCl_3$, $FeCl_3$.

The starting materials of formula IIIa to be used in this process variant can be prepared in a manner known per se. For example, a compound of formula

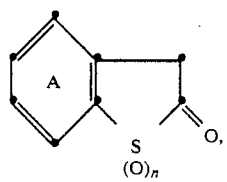

(IIa)

a tautomer or salt thereof, can be reacted with a compound of the formula $X_1$-CO-alk-$X_2$ (IIIc), in which $X_1$ and $X_2$ have the meanings given above, in accordance with the method described in Variant a).

The starting materials of formula IIIb are partially known or can be prepared in a manner known per se.

The invention relates also to the novel compounds obtainable in accordance with the process variants above.

A compound of formula I obtainable in accordance with the invention or by other means can be converted into a different compound of formula I in a manner known per se.

Thio can, for example, be oxidised to corresponding sulfinyl or sulfonyl in customary manner. Suitable oxidising agents for the oxidation to the sulfoxide stage are, for example, inorganic peracids, such as peracids of mineral acids, for example periodic acid or persulfuric acid, organic peracids, such as corresponding percarboxylic or persulfonic acids, for example performic, peracetic, trifluoroperacetic, p-nitroperbenzoic, m-chloroperbenzoic or perbenzoic acid or p-tolueneper-sulfonic acid, or mixtures of hydrogen peroxide and acids, for example a mixture of hydrogen peroxide with acetic acid. The oxidation is frequently carried out in the presence of suitable catalysts, suitable catalysts being suitable acids, such as unsubstituted or substituted carboxylic acids, for example acetic acid or trifluoroacetic acid, or transition metal oxides, such as oxides of elements of subgroup V or VI, for example vanadium, molybdenum or tungsten oxide. The oxidation is carried out under mild conditions, for example at a temperature of from approximately −50° to approximately +100° C. The oxidation to the sulfone stage can also be effected in corresponding manner using dinitrogen tetroxide as catalyst in the presence of oxygen at low temperatures, as may also the direct oxidation of thio to sulfonyl, in which case, however, the oxidising agent is usually used in excess.

Salts of compounds of formula (I) can be prepared in a manner known per se. Thus, for example, salts with bases of free compounds of formula (I) are obtained by treatment with a base or a suitable ion exchange reagent. Salts can be converted into the free compounds in customary manner; for example, salts with bases can be converted by treatment with a suitable acidic agent.

Depending upon the procedure and reaction conditions, the compounds according to the invention having salt-forming, especially acidic, properties may be obtained in free form or in the form of salts, or in the form of tautomers.

As a result of the close relationship between the novel compound in free form and in the form of its salts, hereinbefore and hereinafter the free compound or its salts should be understood as meaning also the corresponding salts or the free compound, respectively, where appropriate and expedient.

The novel free compounds, and their salts, can also be obtained in the form of their hydrates or may include other solvents used for crystallisation.

Depending upon the starting materials and procedures chosen, the novel compounds may be in the form of one of the possible isomers or in the form of a mixture thereof, for example depending upon the number of asymmetric carbon atoms, they may be in the form of pure optical isomers, such as antipodes, or in the form of isomeric mixtures, such as racemates, diastereoisomeric mixtures or mixtures of racemates.

Resulting mixtures of racemates can be separated into the pure isomers or racemates in known manner on the basis of the physico-chemical differences between the constituents, for example by fractional crystallisation. Resulting racemates can be separated into the optical antipodes by known methods, for example by recrystallisation from an optically active solvent, by chromatography on chiral adsorbents, with the aid of suitable microorganisms, by cleaving with specific, immobilised enzymes, by means of the formation of inclusion compounds, for example using chiral Crown ethers, in which case only one enantiomer is complexed, or by conversion into diastereoisomeric salts, for example by reaction of an acidic end product racemate with an optically active base and separation of the mixture of diastereoisomers obtained in this manner, for example on the basis of their different solubilities, into the diastereoisomers from which the desired enantiomer can be freed by the action of suitable agents. Advantageously, the more active enantiomer is isolated.

The invention also relates to those forms of the process according to which a compound obtainable as intermediate at any stage of the process is used as starting material and the remaining steps are carried out, or a starting material is used in the form of a derivative or salt and/or its racemates or antipodes or, especially, is formed under the reaction conditions.

In the process of the present invention it is preferable to use those starting materials which result in the compounds described at the beginning as being especially valuable. The invention relates also to novel starting materials, for example of formulae IIa, IIb, IIIa and IIIb, which have been developed specifically for the preparation of the compounds according to the invention, to their use and to processes for their preparation, the variables having the meanings indicated for the groups of compounds of formula I that are preferred in each case.

The invention relates also to the use of compounds of formulae (I) and (Ia) or pharmaceutically acceptable salts of such compounds having salt-forming properties, especially as pharmacological, more especially analgesically active, active ingredients. They can be used, preferably in the form of pharmaceutically acceptable preparations, in a method for the prophylactic and/or therapeutic treatment of the animal or human body, especially as analgesics, for example for the treatment of pain.

The invention relates also to pharmaceutical preparations that contain as active ingredient the compounds according to the invention or pharmaceutically acceptable salts thereof, and to processes for their manufacture.

The pharmaceutical preparations according to the invention, which contain the compound according to the invention or pharmaceutically acceptable salts thereof, are for enteral, such as oral and rectal, and parenteral, and also topical administration to (a) warm-blooded animal(s), the preparations containing the pharmacological active ingredient on its own or together with a pharmaceutically acceptable carrier.

The novel pharmaceutical preparations contain, for example, from approximately 10% to approximately 80%, preferably from approximately 20% to approximately 60%, active ingredient. Pharmaceutical preparations according to the invention for enteral and parenteral administration are, for example, those in dosage unit forms, such as dragées, tablets, capsules or suppositories, and also ampoules. They are manufactured in a manner known per se, for example by means of conventional mixing, granulating, confectioning, dissolving or lyophilising processes. Thus, pharmaceutical preparations for oral use can be obtained by combining the active ingredient with solid carriers, optionally granulating a resulting mixture, and processing the mixture or granulate, if desired or necessary, after the addition of suitable adjuncts, to form tablets or dragée cores.

Suitable carriers are especially fillers, such as sugars, for example lactose, saccharose, mannitol or sorbitol, cellulose preparations and/or calcium phosphates, for example tricalcium phosphate or calcium hydrogen phosphate, also binders, such as starch pastes using corn, wheat, rice or potato starch, gelatine, tragacanth, methylcellulose and/or polyvinylpyrrolidone, and, if desired, disintegrators, such as the above-mentioned starches, also carboxymethyl starch, cross-linked polyvinylpyrrolidone, agar, alginic acid or a salt thereof, such as sodium alginate. Adjuncts are especially flow-regulating agents and lubricants, for example silica, talc, stearic acid or salts thereof, such as magnesium or calcium stearate, and/or polyethylene glycol. Dragée cores are provided with suitable coatings which may be resistant to gastric juices, there being used, inter alia, concentrated sugar solutions which may contain gum arabic, talc, polyvinylpyrrolidone, polyethylene glycol and/or titanium dioxide, or lacquer solutions in suitable organic solvents or solvent mixtures, or, for the production of coatings resistant to gastric juices, solutions of suitable cellulose preparations, such as acetylcellulose phthalate or hydroxypropylmethylcellulose phthalate. Colourings or pigments may be added to the tablets or dragée coatings, for example for identification purposes or to indicate different doses of active ingredient.

Further orally administrable pharmaceutical preparations are dry-filled capsules consisting of gelatine, and also soft, sealed capsules consisting of gelatine and a plasticiser, such as glycerine or sorbitol. The dry-filled capsules may contain the active ingredient in the form of a granulate, for example in admixture with fillers, such as lactose, binders, such as starches, and/or glidants, such as talc or magnesium stearate, and optionally stabilisers. In soft capsules, the active ingredient is preferably dissolved or suspended in suitable liquids, such as fatty oils, paraffin oil or liquid polyethylene glycols, to which stabilisers may likewise be added.

There come into consideration as rectally administrable pharmaceutical preparations, for example, suppositories that consist of a combination of the active ingredient and a suppository base. Suitable suppository bases are, for example, natural or synthetic triglycerides, paraffin hydrocarbons, polyethylene glycols or higher alkanols. It is also possible to use gelatine rectal capsules that contain a combination of the active ingredient and a base material. Suitable base materials are, for example, liquid triglycerides, polyethylene glycols or paraffin hydrocarbons.

Suitable for parenteral administration are especially aqueous solutions of an active ingredient in water-soluble form, for example a water-soluble salt, and also suspensions of the active ingredient, such as corresponding oily injection suspensions, there being used suitable lipophilic solvents or vehicles, such as fatty oils, for example sesame oil, or synthetic fatty acid esters, for example ethyl oleate or triglycerides, or aqueous injection suspensions that contain viscosity-increasing substances, for example sodium carboxymethylcellulose, sorbitol and/or dextran, and, optionally, also stabilisers.

Pharmaceutical preparations suitable for topical application are especially creams, ointments, foams, tinctures and solutions that contain from approximately 0.5 to approximately 20% active ingredient.

Creams are oil-in-water emulsions that contain more than 50% water. As oily base there are used especially fatty alcohols, for example lauryl, cetyl or stearyl alcohol, fatty acids, for example palmitic or stearic acid, liquid to solid waxes, for example isopropyl myristate, wool wax or beeswax, and/or hydrocarbons, for example petroleum jelly (petrolatum) or paraffin oil. Suitable emulsifiers are surface-active substances having predominantly hydrophilic properties, such as corresponding non-ionic emulsifiers, for example fatty acid esters of polyalcohols or ethylene oxide adducts thereof, such as polyglycerine fatty acid esters or polyoxyethylene sorbitan fatty acid esters (Tweens), and also polyoxyethylene fatty alcohol ethers or fatty acid esters, or corresponding ionic emulsifiers, such as alkali metal salts of fatty alcohol sulfates, for example sodium lauryl sulfate, sodium cetyl sulfate or sodium stearyl sulfate, which are usually used in the presence of fatty alcohols, for example cetyl alcohol or stearyl alcohol. Additives to the aqueous phase are, inter alia, agents that reduce the drying out of the creams, for example polyalcohols, such as glycerine, sorbitol, propylene glycol and/or polyethylene glycols, and also preservatives, perfumes, etc.

Ointments are water-in-oil emulsions that contain up to 70%, but preferably from approximately 20% to approximately 50%, water or aqueous phases. Suitable as fatty phase are especially hydrocarbons, for example petroleum jelly, paraffin oil and/or hard paraffins, which, in order to improve the water-binding capacity, preferably contain suitable hydroxy compounds, such as fatty alcohols or esters thereof, for example cetyl alcohol or wool wax alcohols, or wool wax. Emulsifiers are corresponding lipophilic substances, such as sorbitan fatty acid esters (Spans), for example sorbitan oleate and/or sorbitan isostearate. Additives to the aqueous phase are, inter alia, humectants, such as polyalcohols, for example glycerine, propylene glycol, sorbitol and/or polyethylene glycol, and also preservatives, perfumes, etc.

Fatty ointments are anhydrous and contain as base especially hydrocarbons, for example paraffin, petroleum jelly and/or liquid paraffins, also natural or partially synthetic fat, for example coconut fatty acid triglyceride, or preferably hardened oils, for example hydrogenated groundnut oil or castor oil, also fatty acid partial esters of glycerine, for example glycerine mono- and di-stearate, and also, for example, the fatty alcohols increasing the water-absorption capacity, emulsifiers and/or additives mentioned in connection with the ointments.

Pastes are creams and ointments having secretion-absorbing powder constituents, such as metal oxides, for example titanium oxide or zinc oxide, also talcum and/or aluminium silicates, the purpose of which is to bind any moisture or secretions present.

Foams are administered from pressurised containers and are liquid oil-in-water emulsions in aerosol form; halogenated hydrocarbons, such as chlorofluoro-lower alkanes, for example dichlorodifluoromethane and dichlorotetrafluoroethane, are used as propellants. As oil phase there are used, inter alia, hydrocarbons, for example paraffin oil, fatty alcohols, for example cetyl alcohol, fatty acid esters, for example isopropyl myristate, and/or other waxes. As emulsifiers there are used, inter alia, mixtures of emulsifiers having predominantly hydrophilic properties, such as polyoxyethylenesorbitan fatty acid esters (Tweens) and emulsifiers having predominantly lipophilic properties, such as sorbitan fatty acid esters (Spans). The customary additives, such as preservatives, etc., are also added.

Tinctures and solutions generally have an aqueous-ethanolic base to which there are added, inter alia, polyalcohols, for example glycerine, glycols, and/or polyethylene glycol, as humectants for reducing evaporation, and fat-restoring substances, such as fatty acid esters with low molecular weight polyethylene glycols, that is to say lipophilic substances that are soluble in the aqueous mixture, as a replacement for the fatty substances removed from the skin by the ethanol, and, if necessary, other adjuncts and additives.

The manufacture of the topically administrable pharmaceutical preparations is effected in a manner known per se, for example by dissolving or suspending the active ingredient in the base or, if necessary, in a portion thereof. When the active ingredient is processed in the form of a solution, it is generally dissolved in one of the two phases before emulsification; when the active ingredient is processed in the form of a suspension, it is mixed with a portion of the base before emulsification and then added to the remainder of the formulation.

The dosage of the active ingredient depends upon the species of warm-blooded animal, age and individual condition, and upon the method of administration. In normal cases, the approximate daily dose for a warm-blooded animal weighing about 75 kg is estimated to be, in the case of oral administration, from approximately 100 mg to approximately 1000 mg, advantageously in several equal partial doses.

The following Examples illustrate the invention described above but are not intended to limit the scope thereof in any way. Temperatures are given in degrees Celsius.

EXAMPLE 1

In a sulfonating flask under a nitrogen atmosphere, 15 g of benzo[b]thiophene-2(3H)-one (100 mmol) are dissolved in 150 ml of distilled hexametapol. The light-yellow solution is cooled to 5°. 8.9 g of a sodium hydride suspension (55%) that has been de-oiled with n-hexane are then added in portions while stirring. The resulting suspension is stirred for 15 minutes at 20°, during which time the evolution of gas is observed. The suspension is then cooled to −10° and 17.65 g of 2-(2-thienyl)-acetic acid chloride are added, the internal temperature being maintained at below 0°. After the cooling has been removed, the mixture is stirred for 1 hour. The reaction mixture is poured onto 2 liters of ice-water and 60 ml of 2N hydrochloric acid, and then 500 ml of toluene are added. The separated organic phase is extracted twice with water and then three times using 200 ml of 5% soda solution each time. The alkaline phase is filtered and poured onto ice and 2N hydrochloric acid, and the crystals that are formed are filtered off and dried. Chromatography over silica gel and recrystallisation from methanol yield 2-hydroxy-3-[2-(2-thienyl)-acetyl]-benzo[b]thiophene,

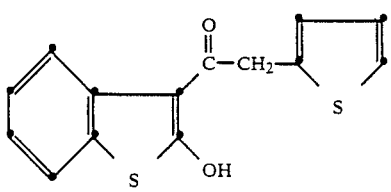

m.p. 99°–101°, which is digested in 100 ml of methanol, and 13.68 ml of 30% sodium methanolate solution are added. After concentration to dryness by evaporation, first 200 ml of ether and then acetone are added. The crystalline sodium salt melts at 201°–204°.

EXAMPLE 2

In a sulfonating flask under a nitrogen atmosphere, 11 g of 5-fluoro-benzo[b]thiophen-2(3H)-one are dissolved in 110 ml of distilled hexametapol. The solution is cooled to 0°. 5.71 g of a sodium hydride suspension (55%) that has been de-oiled with n-hexane are then added in portions while stirring, whereupon gas begins to evolve. The reaction mixture is maintained at 15° and stirred until the evolution of gas has ceased. Then at a temperature of from −5° to 0°, 11.55 g of 2-(2-thienyl)-acetic acid chloride are added dropwise. The internal temperature is increased to 50° and the evolution of gas begins again. After further stirring, the reaction mixture is poured onto 2 liters of ice-water and 50 ml of 2N hydrochloric acid, and 200 ml of toluene are added. The organic phase is extracted twice with water and then three times using 150 ml of 3% soda solution each time. The alkaline solution is filtered and poured onto ice-water and 2N hydrochloric acid. The crystals that are formed are filtered off, dried and, after being dissolved in 300 ml of toluene, chromatographed over silica gel. The crystalline residue, 5-fluoro-2-hydroxy-3-[2-(2-thienyl)-acetyl]-benzo[b]thiophene (m.p. 134°–136°), is digested in 100 ml of methanol, and 8.9 ml of 30% sodium methanolate solution are added. The solution is then concentrated in a rotary evaporator, and the residue is digested with ether and filtered. The residue is dissolved in 50 ml of acetone, poured onto 400 ml of ether and the crystalline residue is filtered and dried in vacuo, thus yielding the sodium salt of 5-fluoro-2-hydroxy-3-[2-(2-thienyl)-acetyl]-benzo[b]thiophene, m.p. 226°–230°.

EXAMPLE 3

In a manner analogous to that described in Example 1 or 2, 6-fluoro-2-hydroxy-3-[2-(2-thienyl)-acetyl]-benzo[b]thiophene can be prepared from 4 g of 6-fluoro-benzo[b]thiophen-2(3H)-one and 4.57 g of 2-(2-thienyl)-acetic acid chloride. The sodium salt, obtained analogously to Example 1 or 2, melts at 264°–268°.

EXAMPLE 4

In a manner analogous to that described in Example 1 or 2, 6-fluoro-2-hydroxy-3-[2-(4-fluorophenyl)-acetyl]-benzo[b]thiophene, m.p. 106°–108°, can be prepared from 4 g of 6-fluoro-benzo[b]thiophen-2(3H)-one and 4.31 g of 2-(4-fluorophenyl)-acetic acid chloride. The sodium salt, obtained analogously to Example 1 or 2, melts at 254°–257°.

EXAMPLE 5

In a manner analogous to that described in Example 1 or 2, 6-fluoro-2-hydroxy-3-(2-phenylacetyl)-benzo[b]thiophene, m.p. 64°–66°, can be prepared from 4 g of 6-fluoro-benzo[b]thiophen-2(3H)-one and 3.86 g of 2-phenylacetyl chloride. The sodium salt, obtained analogously to Example 1 to 2, melts at 270°–275°.

EXAMPLE 6

In a manner analogous to that described in Example 1 or 2, 5-fluoro-2-hydroxy-3-(2-phenylacetyl)-benzo[b]thiophene, m.p. 109°–111°, can be prepared from 5 g of 5-fluoro-benzo[b]thiophen-2(3H)-one and 5.06 g of 2-phenylacetyl chloride. The sodium salt, obtained analogously to Example 1 or 2, melts at 265°–269°.

EXAMPLE 7

In a manner analogous to that described in Example 1 or 2, 2-hydroxy-3-[2-(3-fluorophenyl)-acetyl]-benzo[b]thiophene, m.p. 88°–90°, can be prepared from 10 g of benzo[b]thiophen-2(3H)-one and 12.63 g of 2-(3-fluorophenyl)-acetyl chloride. The sodium salt, obtained analogously to Example 1 or 2, melts at 213°–216°.

EXAMPLE 8

In a manner analogous to that described in Example 1 or 2, 6-fluoro-2-hydroxy-3-[2-(3-trifluoromethylphenyl)-acetyl]-benzo[b]thiophene, m.p. 77°–79°, can be prepared from 5 g of 6-fluoro-benzo[b]thiophen-2(3H)-one and 7.37 g of 2-(3-trifluoromethylphenyl)-acetyl chloride. The sodium salt, obtained analogously to Example 1 or 2, melts at 200°–203°.

EXAMPLE 9

In a manner analogous to that described in Example 1 or 2, 2-hydroxy-3-[2-(4-methoxyphenyl)-acetyl]-benzo[b]thiophene, m.p. 122°–123°, can be prepared from 7.4 g of benzo[b]thiophen-2(3H)-one and 10.01 g of 2-(4-methoxyphenyl)-acetyl chloride. The sodium salt, obtained analogously to Example 1 or 2, melts at 155°–157°.

EXAMPLE 10

In a manner analogous to that described in Example 1 or 2, 2-hydroxy-3-(2-phenylacetyl)-benzo[b]thiophene, m.p. 101°–103°, can be prepared from 7.18 g of benzo[b]thiophen-2(3H)-one and 8.14 g of phenylacetyl chloride. The sodium salt, obtained analogously to Example 1 or 2, melts at 227°–230°.

EXAMPLE 11

In a manner analogous to that described in Example 1 or 2, 2-hydroxy-3-[2-(4-fluorophenyl)-acetyl]-benzo[b]thiophene, m.p. 105°–106°, can be prepared from 7.62 g of benzo[b]thiophen-2(3H)-one and 9.63 g of 2-(4-fluorophenyl)-acetyl chloride. The sodium salt, obtained analogously to Example 1 or 2, melts at 238°–241°.

EXAMPLE 12

In a manner analogous to that described in Example 1 or 2, 2-hydroxy-3-(2-phenylpropionyl)-benzo[b]thiophene, m.p. 82°–83°, can be prepared from 7.13 g of benzo[b]thiophen-2(3H)-one and 9.8 g of 2-phenylpropionyl chloride. The sodium salt, obtained analogously to Example 1 or 2, melts at 153°–156°.

EXAMPLE 13

In a manner analogous to that described in Example 1 or 2, 6-chloro-2-hydroxy-3-[2-(2-thienyl)-acetyl]-benzo[b]thiophene, m.p. 77°–78°, can be prepared from 7.4 g of 6-chloro-benzo[b]thiophen-2(3H)-one and 7.08 g of 2-thiophenacetic acid chloride. The sodium salt, obtained analogously to Example 1 or 2, melts at 211°–214°.

EXAMPLE 14

In a manner analogous to that described in Example 1 or 2 it is possible to prepare:
2-hydroxy-3-[2-(4-chlorophenyl)-acetyl]-benzo[b]thiophene, m.p. 112°–114°; Na salt: m.p. 252°–255°;

5-fluoro-2-hydroxy-3-[2-(2-pyridyl)-acetyl]-benzo[b]-thiophene;

5-fluoro-2-hydroxy-3-[2-(3-pyrrolyl)-acetyl]-benzo[b]-thiophene;

2-hydroxy-3-[2-(2-thienyl)-acetyl]-benzo[b]thiophene 1-oxide;

2-hydroxy-3-[2-(2-thienyl)-acetyl]-benzo[b]thiophene 1,1-dioxide;

2-hydroxy-3-(2-phenylacetyl)-benzo[b]thiophene 1-oxide;

2-hydroxy-3-(2-phenylacetyl)-benzo[b]thiophene 1,1-dioxide.

EXAMPLE 15

In a sulfonating flask under a nitrogen atmosphere, 8.41 g of benzo[b]thiophen-2(3H)-one (100 mmol) are dissolved in 150 ml of distilled hexametapol. The light-yellow solution is cooled to 5°. 8.9 g of a sodium hydride suspension (55%) that has been de-oiled with n-hexane are then added in portions while stirring. The resulting suspension is stirred for 15 minutes at 20°, during which time the evolution of gas is observed. Then at from 30° to 40°, 11.66 g of 2-(4-chlorophenyl)-acetic acid chloride are added dropwise. The mixture is then stirred for 30 minutes at 50°. The reaction mixture is poured onto 2 liters of ice-water and 60 ml of 2N hydrochloric acid, and then 500 ml of toluene are added. The separated organic phase is extracted twice with water and then three times using 200 ml of 5% soda solution each time. The alkaline phase is filtered and poured onto ice and 2N hydrochloric acid; n-hexane is added to the oil that is formed and the mixture is stirred. The crystals that are formed are filtered off, washed with n-hexane/ether (1:1) and dried in vacuo, thus yielding 2-hydroxy-3-[2-(4-chlorophenyl)-acetyl]-benzo[b]thiophene, m.p. 112°-114°, which is digested in 50 ml of methanol, and 5.44 ml of 30% sodium methanolate solution are added at pH 8-9. After concentration to dryness by evaporation, ether is added. The crystalline sodium salt melts at 252°-255°.

EXAMPLE 16

In a sulfonating flask under a nitrogen atmosphere, 3 g of 5-fluoro-benzo[b]thiophen-2(3H)-one are dissolved in 30 ml of distilled hexametapol. The solution is cooled to 0°. 1.63 g of a sodium hydride suspension (55%) that has been de-oiled with n-hexane are then added in portions while stirring, whereupon gas begins to evolve. The reaction mixture is maintained at room temperature for 30 minutes and stirred until the evolution of gas has ceased. Then at an internal temperature of from 35° to 45°, 3.14 g of 2-(3-thienyl)-acetic acid chloride are added dropwise. The internal temperature is increased to 50° and the evolution of gas begins again. After further stirring, the reaction mixture is poured onto 2 liters of ice-water and 50 ml of 2N hydrochloric acid, and 200 ml of toluene are added. The organic phase is extracted twice with water and then three times using 150 ml of 5% soda solution each time. The alkaline solution is filtered and poured onto ice-water and 2N hydrochloric acid. The crystals that are formed are filtered off, dried and washed three times with n-hexane. The crystalline residue, 5-fluoro-2-hydroxy-3-[2-(3-thienyl)-acetyl]-benzo[b]thiophene (m.p. 122°-124°), is digested in 50 ml of methanol, and 2.91 ml of 30% sodium methanolate solution are added. The solution is then concentrated in a rotary evaporator and dried in vacuo. The residue is digested with 30 ml of ether and stirred. Crystals are formed which are filtered off, washed with water and filtered, and dried in vacuo, thus yielding the sodium salt of 5-fluoro-2-hydroxy-3-[2-(3-thienyl)-acetyl]-benzo[b]thiophene, m.p. 278°-281°.

EXAMPLE 17

In a sulfonating flask under a nitrogen atmosphere, 4.83 g of benzo[b]thiophen-2(3H)-one are dissolved in 50 ml of distilled hexametapol. The light-yellow solution is cooled to 5°. 3.09 g of a sodium hydride suspension (55%) that has been de-oiled with n-hexane are then added in portions while stirring. The resulting suspension is stirred for 15 minutes at 20°, during which time the evolution of gas is observed. 14.4 g of 2-(1-methylpyrrol-2-yl)-acetic acid isobutylcarbonic acid anhydride are then added, the internal temperature rising to 31°. The internal temperature is then increased to 60° by means of a water bath. The reaction mixture is then poured onto 2 liters of ice-water and 60 ml of 2N hydrochloric acid, an oil being formed. The oil is extracted twice with ethyl acetate, washed with water and dried over MgSO$_4$. The resulting oil is digested with ether, treated with active carbon and filtered with suction over a Hyflo filter. After the solution has been concentrated by evaporation it is dried in vacuo. The residue is then dissolved in toluene and applied under pressure to a column of silica gel (20 g; conditioned with toluene) at 0.4 bar. The resulting oil is digested in ether and n-hexane, thus yielding 2-hydroxy-3-[2-(1-methylpyrrol-2-yl)-acetyl]-benzo[b]thiophene, m.p. 94°-96°, which is digested in methanol, and 1.2 ml of 30% sodium methanolate solution are added. After concentration to dryness by evaporation, it is digested in ether and stirred. The resulting crystalline sodium salt melts at 249°-253°.

EXAMPLE 18

In a sulfonating flask under a nitrogen atmosphere, 6.44 g of 5-chloro-benzo[b]thiophen-2(3H)-one are dissolved in 50 ml of distilled hexametapol. The solution is cooled to 0°. 3.19 g of a sodium hydride suspension (55%) that has been de-oiled with n-hexane are then added in portions while stirring, whereupon gas begins to evolve. The reaction mixture is maintained at 15° and stirred until the evolution of gas has ceased. At an internal temperature of from 30° to 35°, 6.16 g of 2-(2-thienyl)-acetic acid chloride are then added dropwise. The internal temperature is increased to 50° and the mixture is stirred for 15 minutes. The reaction mixture is poured onto 2 liters of ice-water and 50 ml of 2N hydrochloric acid, and 200 ml of toluene are added. The organic phase is extracted twice with water and then three times using 150 ml of 3% soda solution each time. The alkaline solution is filtered and poured onto ice-water and 2N hydrochloric acid. The crystals that are formed are filtered off, dissolved in methylene chloride and dried over MgSO$_4$. The resulting oil is boiled up with 100 ml of n-hexane. The crystals that are formed are filtered off and dried, thus yielding 5-chloro-2-hydroxy-3-[2-(2-thienyl)-acetyl]benzo[b]thiophene (m.p. 129°-130°). This product is digested in 50 ml of methanol, and 4.38 ml of 30% sodium methanolate solution are added. The solution is then concentrated in a rotary evaporator, and the residue is digested with ether, stirred and filtered. The residue is washed with ether, and the crystalline residue is filtered, and dried in vacuo, thus yielding the sodium salt of 5-chloro-2- hydroxy-3-[2-(2-thienyl)-acetyl]-benzo[b]thiophene, m.p. 258°–261°.

EXAMPLE 19

In a sulfonating flask under a nitrogen atmosphere, 3 g of 5-nitrobenzo[b]thiophen-2(3H)-one are dissolved in 50 ml of distilled hexametapol. The light-yellow solution is cooled to 5°. 1.44 g of a sodium hydride suspension (55%) that has been de-oiled with n-hexane are then added in portions while stirring. The resulting suspension is stirred for 15 minutes at 20°, during which time the evolution of gas is observed. Then at from 30° to 40°, 2.71 g of 2-(2-thienyl)-acetic acid chloride are added and the mixture is stirred at 50° for 15 minutes. The reaction mixture is poured onto 2 liters of ice-water and 60 ml of 2N hydrochloric acid, and then 500 ml of toluene are added. The separated organic phase is extracted twice with water and then three times using 200 ml of 5% soda solution each time. The alkaline phase is filtered and poured onto ice and 2N hydrochloric acid, and the crystals that are formed are filtered off and dried. The crystals are then digested twice with ether, filtered and dried in vacuo, thus yielding 2-hydroxy-5-nitro-3-[2-(2-thienyl)-acetyl]-benzo[b]thiophene, m.p. 128°–130°.

EXAMPLE 20

In an analogous manner, for example as described in one of the preceding Examples, 2-hydroxy-3-[3-(2-thienyl)-propionyl]-benzo[b]thiophene can be prepared from benzo[b]thiophen-2(3H)-one and 3-(2-thienyl)-propionic acid chloride. The sodium salt, obtained analogously to Example 1 or 2, melts at 259°–262°.

EXAMPLE 21

In an analogous manner, for example as described in Example 1 or 2, 2-hydroxy-3-[2-(5-bromo-2-thienyl)acetyl]-benzo[b]thiophene, m.p. 87°–88°, can be prepared starting from 2.03 g of benzo[b]thiophen-2(3H)-one and 3.1 g of 5-bromo-(2-thienyl)-acetyl chloride. The sodium salt, obtained analogously to Example 1 or 2, melts at 214°–217°.

EXAMPLE 22

In an analogous manner, for example as described in Example 1 or 2, 2-hydroxy-3-[2-methyl-2-thienyl-)acetyl]-benzo[b]thiophene, m.p. 82°–84°, can be prepared. The sodium salt, obtained analogously to Example 1 or 2, melts at 237°–240°.

EXAMPLE 23

In an analogous manner, for example as described in one of the preceding Examples, it is possible to prepare the following:
2-hydroxy-3-[2-(2-pyridyl)-acetyl]-benzo[b]thiophene;
5-fluoro-2-hydroxy-3-[2-(2-thiazolyl)-acetyl]-benzo[b]thiophene;
5-fluoro-2-hydroxy-3-[2-(3-methyl-2-pyridyl)-acetyl]-benzo[b]thiophene;
2-hydroxy-3-[2-(4-chloroimidazol-1-yl)-acetyl]-benzo[b]thiophene;
2-hydroxy-3-[2-(3-bromo-2-pyridyl)-acetyl]-benzo[b]thiophene;
5-fluoro-2-hydroxy-3-[2-(imidazol-2-yl)-acetyl]-benzo[b]thiophene.

EXAMPLE 24

Tablets containing 25 mg of active ingredient, for example the sodium salt of 5-fluoro-2-hydroxy-3-[2-(2-thienyl)-acetyl]-benzo[b]thiophene, can be manufactured as follows:

| Constituents (for 1000 tablets): | |
|---|---|
| active ingredient | 25.0 g |
| lactose | 100.7 g |
| wheat starch | 7.5 g |
| polyethylene glycol 6000 | 5.0 g |
| talcum | 5.0 g |
| magnesium stearate | 1.8 g |
| demineralised water | q.s. |

PREPARATION

All the solid ingredients are first forced through a sieve of 0.6 mm mesh width. Half of the starch is then mixed in. The other half of the starch is suspended in 40 ml of water and this suspension is added to a boiling solution of the polyethylene glycol in 100 ml of water and processed with the powder mixture to form a kneadable mass, and the resulting mixture is granulated, if necessary with the addition of water. The granulate is dried overnight at 35°, forced through a sieve of 1.2 mm mesh width and compressed to form tablets of approximately 6 mm diameter that are concave on both sides.

EXAMPLE 25

In a manner analogous to that described in Example 24, it is also possible to manufacture tablets each containing 25 mg of another of the compounds mentioned in Examples 1 to 23.

What is claimed is:

1. A benzo[b]thiophene derivative of formula

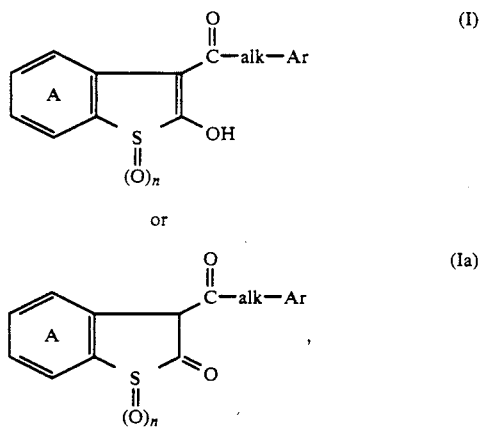

respectively, or a salt thereof, in which n is 0, 1 or 2, alk is lower alkylene, Ar is triazinyl which is unsubstituted or is mono- or poly-substituted by lower alkyl, halo-lower alkyl, halogen or nitro, and ring A is unsubstituted or is mono- or poly-substituted by lower alkyl, lower alkoxy, lower alkylthio, lower alkanesulfinyl, lower alkanesulfonyl, halo-lower alkyl, halogen or nitro.

2. A compound according to claim 1 in which alk is —CH(R)— and R is hydrogen or lower alkyl.

3. A pharmaceutical composition containing a therapeutically effective amount of a compound as claimed in claim 1 or a pharmaceutically acceptable salt thereof and a pharmaceutically acceptable exipient or carrier.

4. A method for the treatment of pain and inflammation in a patient in need thereof comprising administering to said patient a therapeutically effective amount of a compound according to claim 1 or a pharmaceutically acceptable salt thereof.

* * * * *